(12) United States Patent
Klein

(10) Patent No.: US 9,994,677 B2
(45) Date of Patent: Jun. 12, 2018

(54) METHODS AND COMPOUNDS FOR PRODUCING NYLON 12

(71) Applicant: EMPIRE TECHNOLOGY DEVELOPMENT LLC, Wilmington, DE (US)

(72) Inventor: Josef Peter Klein, Vashon, WA (US)

(73) Assignee: EMPIRE TECHNOLOGY DEVELOPMENT LLC, Wilmington, DE (US)

( * ) Notice: Subject to any disclaimer, the term of this patent is extended or adjusted under 35 U.S.C. 154(b) by 0 days. days.

(21) Appl. No.: 15/125,576

(22) PCT Filed: Mar. 11, 2014

(86) PCT No.: PCT/US2014/023301
§ 371 (c)(1),
(2) Date: Sep. 12, 2016

(87) PCT Pub. No.: WO2015/137923
PCT Pub. Date: Sep. 17, 2015

(65) Prior Publication Data
US 2017/0002142 A1    Jan. 5, 2017

(51) Int. Cl.
*C08G 69/00* (2006.01)
*C07D 307/68* (2006.01)

(52) U.S. Cl.
CPC .......... *C08G 69/00* (2013.01); *C07D 307/68* (2013.01)

(58) Field of Classification Search
CPC .............................. C07D 307/69; C08G 69/00
See application file for complete search history.

(56) References Cited

U.S. PATENT DOCUMENTS

| | | | |
|---|---|---|---|
| 5,530,148 A | 6/1996 | Nwaonicha et al. | |
| 6,423,768 B1 | 7/2002 | Khouri | |
| 6,538,099 B2 | 3/2003 | Isobe et al. | |
| 7,776,996 B2 | 8/2010 | Deininger et al. | |
| 8,288,459 B2 | 10/2012 | Iwamoto | |
| 8,324,376 B2 | 12/2012 | Binder et al. | |
| 2010/0317822 A1 | 12/2010 | Boussie et al. | |
| 2014/0005353 A1* | 1/2014 | Yutaka ................... | C08G 69/26 528/341 |

FOREIGN PATENT DOCUMENTS

| | | |
|---|---|---|
| CN | 102295511 A | 12/2011 |
| CN | 103113577 A | 5/2013 |
| GB | 924422 A | 4/1963 |
| WO | 2008138568 A1 | 11/2008 |
| WO | 2011043661 A1 | 4/2011 |
| WO | 2012132792 A1 | 10/2012 |
| WO | 2013034305 A1 | 3/2013 |

OTHER PUBLICATIONS

Buntara et al (Caprolactam from Renewable Resources: Catalytic Conversion of 5-Hydroxymethylfurfural into Caprolactone, Angew. Chem. Int. Ed. 2011, 50, 7083-7087), published on Nov. 2011.*
Ayorinde, F.O., et al., "Syntheses of 12-aminododecanoic and 11-aminoundecanoic acids from vernolic acid," Journal of the American Oil Chemists' Society, vol. 74, Issue 5, pp. 531-538 (May 1997).
Guang, L., et al., "Chemocatalytic biomass-based compounds to transportation fuels," Renewable Energy Resources, vol. 30, No. 4, pp. 62-69 (Apr. 2012) (See English Abstract).
Jiang-Long, G., et al., "Review on production of high-value chemicals and transportation fuels from furfural," Renewable Energy Resources, vol. 31, No. 8, pp. 75-81 (Aug. 2013) (See English Abstract).
Kumari, N., et al., "Synthesis of 5-Bromomethylfurfural from Cellulose as a Potential Intermediate for Biofuel," European Journal of Organic Chemistry, vol. 7, pp. 1266-1270 (Mar. 2011).
Saha, B., et al., "Aerobic oxidation of 5-hydroxylmethylfurfural with homogeneous and nanoparticulate catalysts," Catalysis Science & Technology, vol. 2, pp. 79-81 (Sep. 23, 2011).
Škorić, I., et al., "Synthesis of the novel conjugated w,w'-diaryl/heteroaryl hexatriene system with the central double bond in a heteroaromatic ring: photochemical transformations of 2,3-divinylfuran derivatives," Tetrahedron, vol. 62, pp. 7396-7407 (Jun. 5, 2006).
Su, H., et al., "Design, synthesis and biological evaluation of novel compounds with conjugated structure as anti-tumor agents," Bioorganic & Medicinal Chemistry, vol. 16, pp. 7992-8002 (Jul. 29, 2008).
Zhang, X., et al., "Hydrolysis and Application of Cellulose Biomass," Zhengzhou University, pp. 100-103 (Dec. 31, 2012).
Brasholz et al., Highly efficient dehydration of carbohydrates to 5-(chloromethyl)furfural (CMF), 5-(hydroxymethyl) furfural (HMF) and levulinic acid by biphasic continuous flow processing, Green Chemistry, The Royal Society of Chemistry (Mar. 11, 2011), 13(5) pp. 1114-1117.
Dangerfield et al., Protecting-Group-Free Synthesis of Amines: Synthesis of Primary Amines from Aldehydes via Reductive Amination, Journal of Organic Chemistry, American Chemical Society (Jul. 28, 2010), 75(16) pp. 5470-5477.
International Search Report and Written Opinion for International Application No. PCT/US2014/023301 dated Jun. 2, 2014, pp. 6.
Lewkowski, Synthesis, chemistry and applications of 5-hydroxymethylfurfural and its derivatives, General Papers, Archive for Organic Chemistry (2001), 2001(1) pp. 17-54.

(Continued)

*Primary Examiner* — Gregory Listvoyb

(57) ABSTRACT

Nylon 12 may be produced by dimerization of 6-carbon furan compounds into 12-carbon dimers, and conversion of the dimers into nylon 12. The 6-carbon furan compounds may be produced from biomass. Ester-aldehyde dimers and amino-ester dimers may be produced from the 6-carbon furan compounds as precursors for at least the production of nylon 12, and the components for producing the nylon 12 may be provided as a kit.

28 Claims, 2 Drawing Sheets

(56) References Cited

OTHER PUBLICATIONS

Lichtenthaler, Carbohydrates as Organic Raw Materials, Ullmann's Encyclopedia of Industrial Chemistry (2012), (6) pp. 583-616.
Mascal and Nikitin, Direct, high-yield conversion of cellulose into biofuel, Angewandte Chemie International Edition (Sep. 29, 2008), 47(41) pp. 7924-7926.
Mascal and Nikitin, Dramatic advancements in the saccharide to 5-(chloromethyl)furfural conversion reaction, ChemSusChem (Sep. 21, 2009), 2(9) pp. 859-861.
Mascal and Nikitin, Towards the efficient, total glycan utilization of biomass, ChemSusChem (May 25, 2009), 2(5) pp. 423-426.
Mei et al., TEMPO-Mediated Oxidation of Primary Alcohols to Carboxylic Acids by Exploitation of Ethers in an Aqueous-Organic Biphase System, Bulletin of the Chemical Society of Japan (2009), 82(8) pp. 1000-1002.
Saikachi et al., Synthesis of Furan Derivatives. LV. Macrocyclic Rings from the Reaction of Dialdehyde with Bisphosphorane and with Diamine, Chemical & Pharmaceutical Bulletin (Jan. 1971), 19(1) pp. 97-103.
Yang et al., Conversion of biomass into 5-ydroxymethylfurfural using solid acid catalyst, Bioresource Technology (Feb. 2011), 102(3) pp. 3424-3429.
Zakrzewska et al., Ionic Liquid-Mediated Formation of 5-Hydroxymethylfurtural—A Promising Biomass-Derived Building Block, Chemical Reviews (Oct. 25, 2010), 111(2) pp. 397-417.
"RN 22593-15-3", Registry, STN Columbus, pp. 2 (Nov. 16, 1984).

\* cited by examiner

METHODS AND COMPOUNDS FOR PRODUCING NYLON 12

CROSS-REFERENCE TO RELATED APPLICATION

This application is a U.S. national stage filing under 35 U.S.C. § 371 of International Application No. PCT/US2014/023301 filed on Mar. 11, 2014 entitled "METHODS AND COMPOUNDS FOR PRODUCING NYLON 12," which is incorporated herein by reference in its entirety.

BACKGROUND

Nylon is a designation for a family of synthetic polymers known as aliphatic polyamides, and is one of the most commonly used polymers. The chemical constituents of nylon include carbon, hydrogen, nitrogen, and oxygen. Types of nylons include nylon 6,6, that may be formed by reacting a diamine and a dicarboxylic acid so that amides are formed at both ends of each monomer, nylon 6 that may be made by a ring-opening polymerization of cyclic amides (lactams), and nylon 12 that may be produced from cyclododecatriene.

Nylons are designated by a numerical suffix that specifies the numbers of carbons donated by the monomers. For example, for nylons with a two-number designation, such as nylon 6,6 or nylon 6,12, the first number represents the number of carbons from the diamine monomer, and the second number represents the number of carbons from the diacid monomer. For nylons having a single number designation, such as nylon 12, the number represents the number of carbon atoms in the repeating monomer units.

Nylon 12 (polyamide 12) is a major component of tubings used in automotive brake and fuel lines. Nylon 12 has generally been produced from cyclododecatriene by converting the cyclododecatriene to laurolactam, which is a starting monomer for industrial production of nylon 12. Cyclododecatriene may be produced from butadiene as the raw material. In one method for the production of butadiene that may be considered non-environmentally friendly, the butadiene is derived from petroleum products. Further, an explosion in 2012 at an Evonik Industries plant in Germany that produces a large proportion of the world's supply of cyclododecatriene, resulted in a shortage of the starting materials, and generated concerns over a potential shortage of nylon 12 with the potential of halting of new automobile assembly worldwide.

Thus, there remains a need for environmentally friendly, scalable and cost competitive alternative approaches for producing nylon 12. The alternative approaches should utilize raw materials and methods that are environmentally friendly instead of relying on petrochemically derived raw materials. Such alternative approaches may additionally alleviate concerns over future problems with current production methods, such as that caused by the Evonik Industries explosion.

SUMMARY

Nylon 12 may be produced by dimerization of 6-carbon furan compounds into 12-carbon dimers, and conversion of the dimers into nylon 12. The 6-carbon furan compounds may be produced from biomass. Ester-aldehyde dimers and amino-ester dimers may be produced from the 6-carbon furan compounds as precursors for at least the production of nylon 12.

In an embodiment, a method for producing nylon 12, includes converting alkyl furan compounds of formula

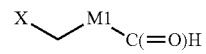

to an ester-aldehyde dimer of formula

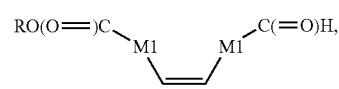

wherein X is —OH or halogen, R is $C_1$-$C_5$ alkyl, and M1 is

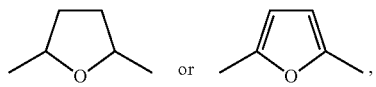

converting the ester-aldehyde dimer to an amino-ester of formula

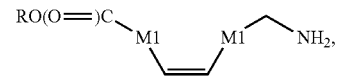

and converting the amino-ester to nylon 12.

In an embodiment, a method for producing nylon 12 from waste stream biomass includes converting the biomass to 5-chloromethylfurfural and 5-hydroxymethylfurfural, and using the 5-chloromethylfurfural and 5-hydroxymethylfurfural as reactants for producing the nylon 12.

In an embodiment, a kit for the production of nylon 12 includes a furan dimer compound of formula

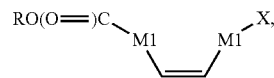

wherein R is $C_1$-$C_5$ alkyl, M1 is

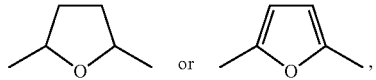

and X is —CHO or —$CH_2$—$NH_2$; a halide source; and a catalyst.

In an embodiment, a furan dimer compound has a formula

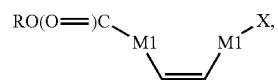

wherein R is $C_1$-$C_5$ alkyl, M1 is

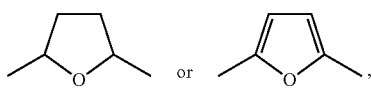

and X is —CHO or —$CH_2$—$NH_2$.

DETAILED DESCRIPTION

Nylon 12 receives its numerical designation from the number of carbon atoms in its monomer units, wherein each monomer unit has twelve carbons as illustrated,

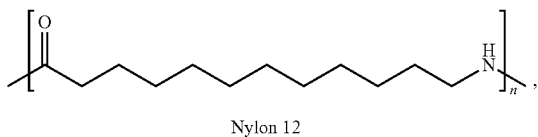

Nylon 12 and n is about 2 to about 1000. In accordance with embodiments as discussed herein, nylon 12 may be produced from 6-carbon compounds by methods that are also environmentally friendly.

Figure 1:
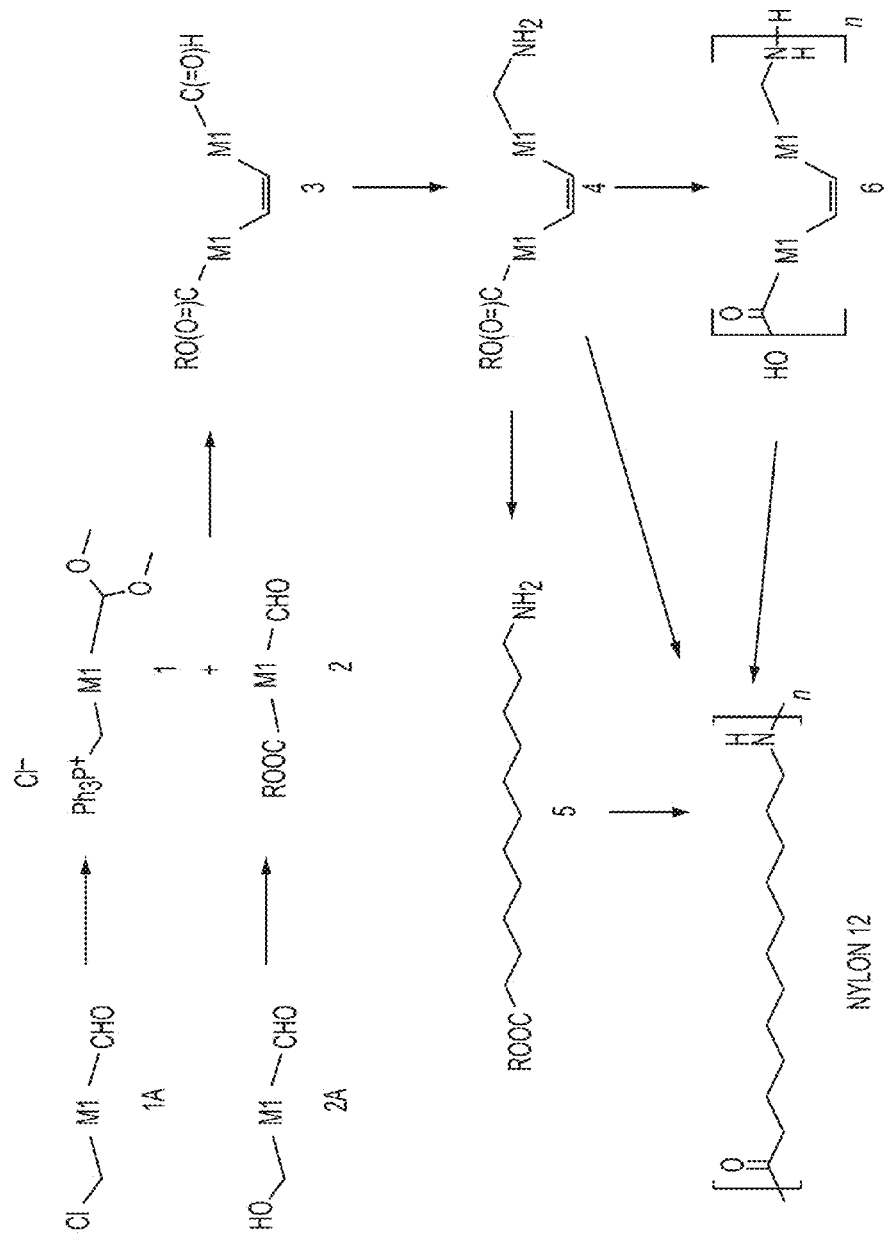
FIG. 1 depicts a general flow diagram for an illustrative method for the production of nylon 12 according to an embodiment.

A representation of a method for producing nylon 12 is depicted in FIG. 1. In an embodiment, alkyl furan compounds 1A and/or 2A of formula

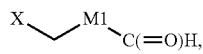

wherein X is —OH or halogen, and M1 is

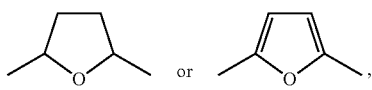

may be converted to ester-aldehyde dimers 3 of formula

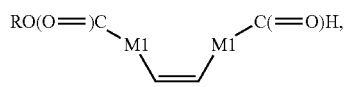

wherein R is $C_1$-$C_5$ alkyl. The dimers 3 may be converted to amino-esters 4 of formula

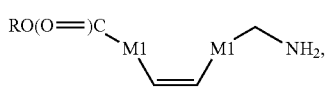

and the amino-esters may be converted to nylon 12.

In an embodiment, the amino-esters 4 may be converted to nylon 12 by a hydrogenation-hydrodeoxygenation-polymerization reaction. One type of hydrogenation-hydrodeoxygenation-polymerization reaction may include treating the amino-ester 4 with a halide source and hydrogen gas in the presence of a catalyst. The halide source may be a hydrogen halide, or combination of hydrogen halides. Hydrogen halides may include hydrogen iodide, hydrogen chloride, and hydrogen bromide, or any combination thereof. The catalyst may include platinum catalysts, palladium catalysts, rhodium catalysts, ruthenium catalysts, nickel catalysts, cobalt catalysts, iron catalysts, molybdenum catalysts, iridium catalysts, rhenium catalysts, or gold catalysts, or any combination thereof. In an embodiment, the catalyst may be mounted on a support.

The conversion of amino-ester 4 to nylon 12 may proceed via any of the three depicted pathways represented in FIG. 1. In a first possible reaction, the hydrogenation-hydrodeoxygenation may take place prior to polymerization to open the furan rings M1 and produce an amino-acid or amino-ester monomer 5. Polymerization of the amino-acid or the amino-ester monomer may then occur to produce the nylon 12. In a second possible reaction, polymerization may take place prior to the hydrogenation-hydrodeoxygenation to form a polymer 6 that contains furan rings M1. Alternatively, the hydrogenation-hydrodeoxygenation and polymerization may occur simultaneously to form nylon 12 directly from the amino-ester 4.

For reactions wherein M1 of the amino-ester 4 may be

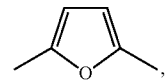

the intermediary amino-ester monomer 5 may be represented by

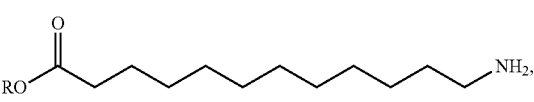

and the polymer 6 may be represented by

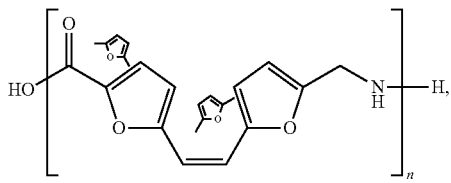

wherein n is about 2 to about 1000.

For reactions wherein M1 of the amino-ester 4 may be

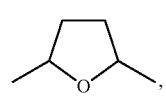

the intermediary amino-ester monomer 5 may be represented by

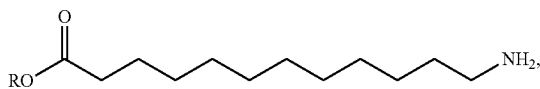

and the polymer 6 may be represented by

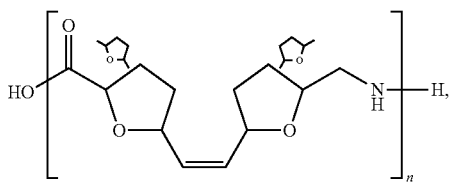

wherein n is about 2 to about 1000.

The starting materials for producing nylon 12, alkyl furan compounds 1A and/or 2A, may be produced from biomass. In an embodiment, the alkyl furan compounds 1A and/or 2A may be produced from biomass by isolating hexoses (glucose and/or fructose), sucrose, cellulose, or corn stover, or any combination thereof from the biomass, and converting the hexoses, sucrose, cellulose, or corn stover, or any combination thereof to the alkyl furan compounds. In an embodiment, nylon 12 may be produced from waste stream biomass. The biomass may be lignocellulosic biomass, and the biomass may be obtained from waste streams of a variety of other processes, such as, for example, waste wood chips and sawdust from lumber and paper production.

In an embodiment, the alkyl furan compound 1A may be 5-chloromethylfurfural, wherein M1 is

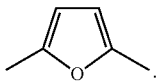

The 5-chloromethylfurfural may be produced from biomass by heating the hexoses, sucrose, cellulose, sugarcane bagasse, or corn stover, or any combination thereof in the presence of at least one solvent. Some examples of the solvent may include, but are not limited to, a mixture of 1,2-dichloroethane and hydrochloric acid, or a mixture of dichloromethane and hydrochloric acid. The reaction may be carried out in the presence of an alkaline salt. Some examples of alkaline salts may include, but are not limited to, lithium halide, sodium halide, or potassium halide, or any combination thereof.

In an embodiment, the alkyl furan compound 2A may be 5-hydroxymethylfurfural wherein M1 is

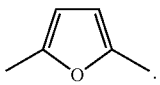

The 5-hydroxymethylfurfural may be produced from biomass by heating the hexoses, or cellulose, or any combination thereof in the presence of at least one of an acid and a metal salt catalyst.

To prepare reactants for the production of the ester-aldehyde dimers 3, alkyl furan compounds 1A, may be converted to dimethylacetal protected Wittig reagents 1 of formula

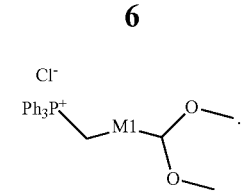

In addition, furan compounds 2A may be oxidized to produce carboxylic acids of formula

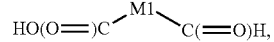

and the carboxylic acid may be alkylated to produce carboxylic acid alkyl esters 2 of formula $$RO(O{=})C^{M1}\diagdown C({=}O)H.$$

The Wittig reagents 1 may be reacted with the carboxylic acid alkyl esters 2 to produce the ester-aldehyde dimers 3.

The 5-chloromethyl furan compounds 1A may be converted to the dimethylacetal protected Wittig reagents 1 by treating the 5-chloromethyl furan compounds with triphenylphosphine, triarylphosphine, trialkyphosphine, or diarylalkylphosphine, or any combination thereof, followed by reaction with an alcohol in the presence of an acid catalyst. The alcohol may be, but is not limited to, methanol, ethanol, propanol, or ethylene glycol, or any combination thereof. The acid catalyst may be, but is not limited to, hydrochloric acid, sulfuric acid, methanesulfonic acid, or toluenesulfonic acid, or any combination thereof.

The 5-hydroxymethyl furan compounds 2A may be oxidized under phase transfer conditions with 4-benzoyloxy-2,2,6,6-tetramethylpiperidin-1-oxyl to produce the intermediary carboxylic acid. Alternatively, the 5-hydroxymethyl furan compounds 2A may be oxidized by electrochemical oxidation. The carboxylic acid may be alkylated by treating the carboxylic acid with an alkyl alcohol and at least one of toluenesulfonic acid, sulfuric acid, and methanesulfonic acid to produce a corresponding alkyl ester dimethylacetal, that may then be treated with aqueous acid to produce the carboxylic acid alkyl ester 2.

In an additional reaction sequence, the ester-aldehyde dimer 3 may be converted to the amino-ester 4. In an embodiment, this may be carried out by aminating the ester-aldehyde dimer 3 with at least one of ammonium hydroxide, ammonia, and hydroxylamine in the presence of hydrogen and a catalyst. The catalyst may include nickel catalysts. In an alternative embodiment, the ester-aldehyde dimer 3 may be converted to the amino-ester 4 by treating the ester-aldehyde with hydroxylamine to produce a corresponding ester-oxime, treating the ester-oxime with hydrogen and a nickel catalyst to produce the amino-ester. In another alternative embodiment, the ester-aldehyde dimer 3 may be converted to the amino-ester 4 by reductive amination of the ester-aldehyde. The reductive amination may include treating the ester-aldehyde with a mixture of sodium cyanoborohydride, ammonium acetate, aqueous ammonium hydroxide and an alcohol. The alcohol may include, but is not limited to, methanol, ethanol, propanol, butanol, or pentanol, or any combination thereof.

In embodiments, some manufacturers and/or users of nylon 12 for products or portions of articles of manufacture, may want to produce the nylon 12 on site. The ester-aldehyde dimers 3 or the amino-ester dimers 4 may be provided as precursor materials for the production of nylon 12. The components for the production of nylon 12 may be provided as a kit. In an embodiment, a kit for the production of nylon 12 may include the amino-ester dimer and additional reactants for the hydrogenation/hydrodeoxygenation/polycondensation of the amino-ester dimer. The additional reactants may include hydrogen iodide as a halide source, and a platinum catalyst mounted on a support, and the components may be pre-measured and ready for the hydrogenation/hydrodeoxygenation/polycondensation reaction.

In an embodiment for producing nylon 12, M1 may be

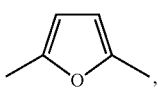

and R may be methyl. In preliminary reaction stages, 5-chloromethylfurfural (CMF in FIG. 2) may be converted to dimethylacetal protected Wittig reagent 11 of formula

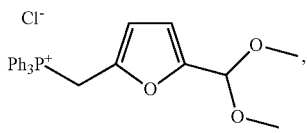

and 5-hydroxymethylfurfural (HMF in FIG. 2) may be oxidized to form 5-formylfuroic acid, that may then be methylated to produce methyl 5-formylfuroate 12 of formula

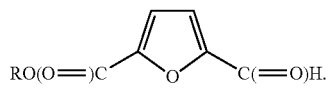

The Wittig reagent 11 may be reacted with the methyl 5-formylfuroate 12 to produce ester-aldehyde dimers 13 of formula

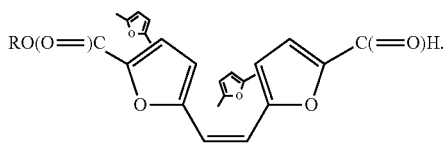

The ester-aldehyde dimers 13 may be converted to amino-esters by amination of the ester-aldehyde to produce amino-esters 14 of formula

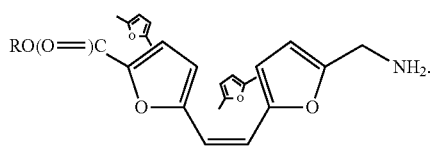

The amino-esters 14 may be converted to nylon 12 by a single-pot hydrogenation-hydrodeoxygenation-polymerization reaction via intermediary products of the amino-esters 15 of formula

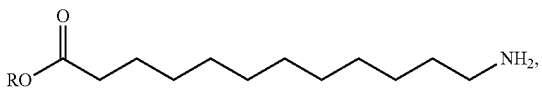

and polymers 16 of formula

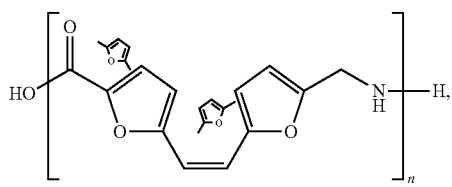

where n≥1.

Figure 2:
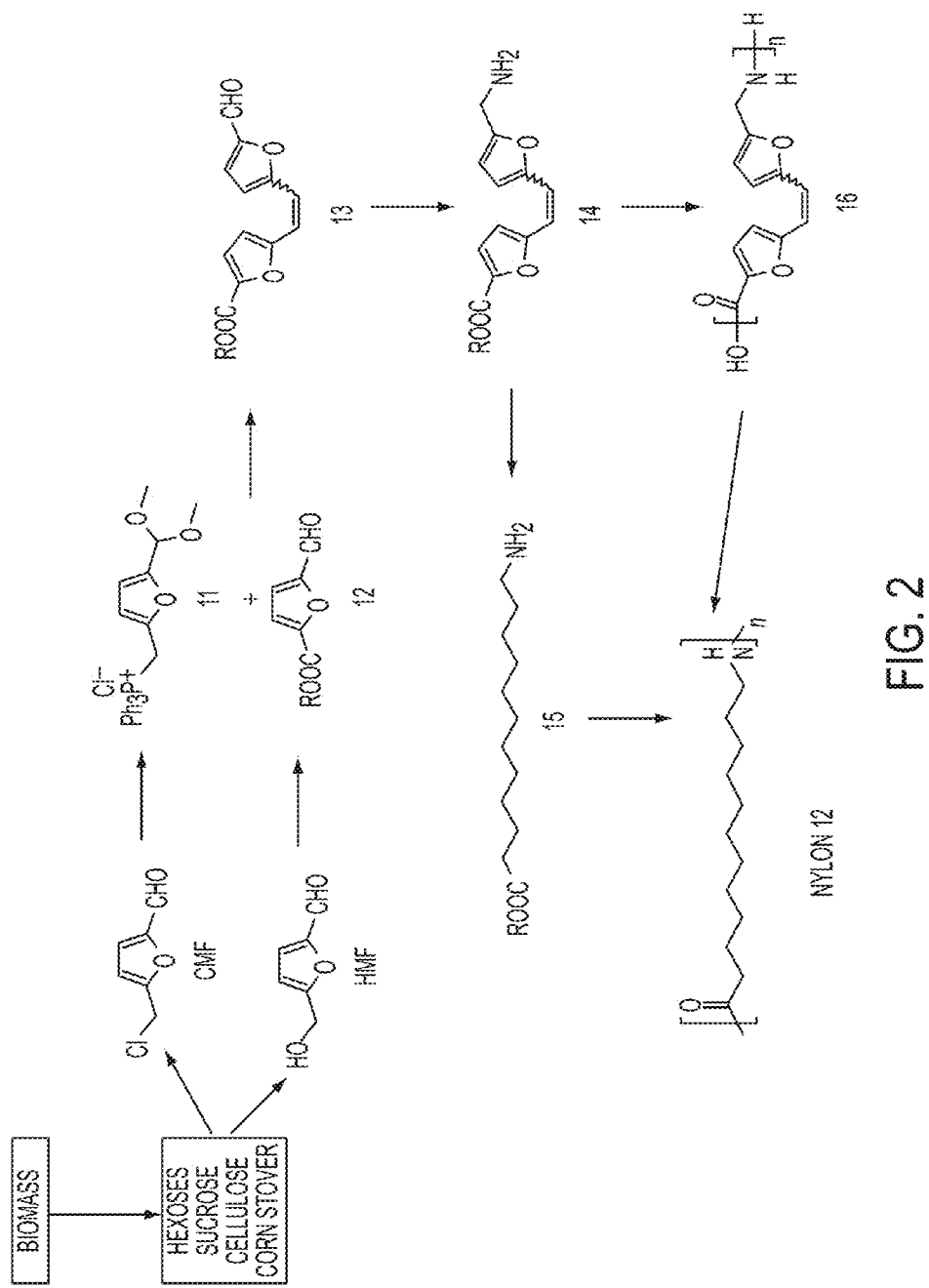
FIG. 2 depicts a diagram for an illustrative method for the production of nylon 12 from waste stream products according to an embodiment.

As mentioned herein, nylon 12 may be produced from waste stream biomass, and, as represented in FIG. 2, a method for producing nylon 12 from waste stream biomass may include converting the biomass to 5-chloromethylfurfural and 5-hydroxymethylfurfural, and using the 5-chloromethylfurfural and 5-hydroxymethylfurfural as reactants for producing nylon 12.

EXAMPLES

Example 1: Ester Precursors for Production of Nylon 12

Ester-aldehyde dimers and amino-ester dimers are produced from 6-carbon furan compounds as precursors for at least the production of nylon 12, as well as other alternative uses.

A mixture of 5-chloromethyl furfural (CMF, 1 equivalent) and triphenylphosphine (1 equivalent) in dry toluene is heated under reflux for about 2 hours. After cooling, the solid is filtered and rinsed with dry toluene to provide [(5-formyl-2-furanyl)methyl]triphenylphosphonium chloride. A mixture of this phosphonium chloride (1 equivalent), trimethyl orthoformate (1.75 equivalents), and p-toluenesulfonic acid (0.001 equivalent) in dry methanol is heated under reflux for about 3 hours. After cooling, sodium acetate (0.002 equivalent) is added and the mixture is concentrated under reduced pressure. Toluene is added and the precipitate is filtered to yield Wittig reagent 11.

A mixture of 5-hydroxymethyl furfural (HMF, 1 equivalent), potassium methoxide (0.25 equivalent), gold on titanium oxide catalyst (0.005 equivalent gold) and methanol is treated with oxygen gas (1 atmosphere) for about 24 hours. The catalyst is removed by filtration and rinsed with methanol. The combined filtrates are concentrated under reduced pressure to yield methyl 5-(hydroxymethyl)-2-furoate. A mixture of methyl 5-(hydroxymethyl)-2-furoate (1 equivalent), o-iodoxybenzoic acid (3 equivalents), and ethyl acetate as solvent, is heated under reflux for about 3 hours. Byproducts are removed by filtration, and the filtrate is concentrated under reduced pressure to yield methyl 5-formyl-2-furoate 12 (R=Me).

To a solution of Wittig reagent 11 (1 equivalent) and methyl 5-formyl-2-furoate 12 (R=Me) (1 equivalent) in dry methanol is added a solution of lithium methoxide in dry methanol at a rate that maintains the reaction temperature below about 35° C. After being stirred for about 3 hours, the mixture is concentrated under reduced pressure. The residue is treated with water and extracted with toluene. The extract is dried over magnesium sulfate and concentrated under reduced pressure. Diethyl ether is added to precipitate and triphenylphosphine oxide byproduct is removed by filtration. The filtrate is concentrated under reduced pressure and the residue is treated with 5% hydrochloric acid in 70% aqueous methanol. After being stirred for about 3 hours, the mixture is neutralized by addition of saturated aqueous sodium bicarbonate solution, and then concentrated under reduced pressure to remove the methanol. The aqueous mixture is extracted with toluene. The extract is washed with water, dried over magnesium sulfate, and concentrated under reduced pressure to provide ester-aldehyde dimer 13 as a mixture of cis and trans isomers. The ester-aldehyde dimer 13 may be provided as a precursor for production of nylon 12, as well as other potential uses.

A mixture of ester-aldehyde dimer 13 (1 equivalent), hydroxylamine hydrochloride (1 equivalents), potassium acetate (1 equivalents) and 50% aqueous ethanol is heated at about 50° C. for about 1 hour. After cooling, the precipitate is filtered, washed with water and dried under reduced pressure to yield the corresponding oxime derivative of ester-aldehyde dimer 13. The oxime derivative of the ester-aldehyde dimer 13 may be provided as a precursor for production of nylon 12, as well as other potential uses.

A mixture of the oxime derivative of ester-aldehyde dimer 13, Raney nickel catalyst, and tetrahydrofuran as solvent is treated with hydrogen gas (50 bar) in an autoclave for about 1 hour. The catalyst is removed by filtration and rinsed with tetrahydrofuran under argon. The combined filtrates are concentrated under reduced pressure to yield amino-ester dimer 14 (R=Me). The amino-ester dimer 14 (R=Me) may be provided as a precursor for production of nylon 12, as well as other potential uses.

Example 2: A Kit for the Production of Nylon 12

A kit for the production of nylon 12 will include the amino-ester dimer 14 (R=Me) and additional reactants for the hydrogenation/hydrodeoxygenation/polycondensation of the amino-ester dimer 14 (R=Me). The additional reactants will include at least hydrogen iodide as a halide source, and a palladium catalyst mounted on silica. The kit may also include acetic acid and hydrogen gas.

Example 3: Production of Nylon 12

The products of the kit of Example 2 will be used to produce nylon 12. A mixture of amino-ester dimer 14 (1 equivalent), 5% palladium on silica (0.01 equivalent palladium), and acetic acid solvent is heated in an autoclave at about 160° C. while treating with hydrogen (about 50 atmospheres pressure) for about 3 hours. The mixture is cooled, hydrogen iodide (1 equivalent) is added, and the mixture is again heated at about 160° C. while treating with hydrogen (about 50 atmospheres) for about 3 hours. The mixture is cooled, and then filtered to remove the catalyst. The solvent is removed by distillation under reduced pressure to yield methyl 12-aminododecanoate. The methyl 12-aminododecanoate is heated at about 270° C. for about 5 hours to provide nylon 12.

Example 4: Generation of Nylon 12 Reactants from Waste Stream Products

Nylon 12 may be produced by the process described in Examples 1-3 from 5-hydroxymethylfurfural and 5-chloromethylfurfural derived from waste stream biomass. Lignocellulosic biomass materials, such as corn stover, sugarcane bagasse, wood chips and sawdust will be obtained from a paper mill, or other waste streams. The biomass will be processed to isolate hexoses, glucose and fructose from the biomass. For 5-hydroxymethylfurfural, the hexoses will be dehydrated by heating the hexoses in the presence of at least one of an acid and a metal salt catalyst to form the 5-hydroxymethylfurfural. For 5-chloromethylfurfural, the hexoses will be chlorinated by heating in the presence of 1,2-dichloroethane and an acid to produce the 5-chloromethyl furfural.

The examples demonstrate that nylon 12 may be produced from waste products in only a few process steps with high yields, thereby providing an alternative and environmentally friendly method for the production of nylon 12 that does not require petrochemically derived raw materials. The disclosed approach is unlikely to suffer from an explosion risk as is associated with production of the nylon 12 precursor cyclododecatriene.

This disclosure is not limited to the particular systems, devices and methods described, as these may vary. The terminology used in the description is for the purpose of describing the particular versions or embodiments only, and is not intended to limit the scope.

In the above detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be used, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds, compositions or biological systems, which can, of course, vary. It is also to be understood that the terminology used herein is for the purpose of describing particular embodiments only, and is not intended to be limiting.

As used in this document, the singular forms "a," "an," and "the" include plural references unless the context clearly dictates otherwise. Unless defined otherwise, all technical and scientific terms used herein have the same meanings as commonly understood by one of ordinary skill in the art. Nothing in this disclosure is to be construed as an admission that the embodiments described in this disclosure are not entitled to antedate such disclosure by virtue of prior invention. As used in this document, the term "comprising" means "including, but not limited to."

While various compositions, methods, and devices are described in terms of "comprising" various components or steps (interpreted as meaning "including, but not limited to"), the compositions, methods, and devices can also "consist essentially of" or "consist of" the various components and steps, and such terminology should be interpreted as defining essentially closed-member groups.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

Various of the above-disclosed and other features and functions, or alternatives thereof, may be combined into many other different systems or applications. Various presently unforeseen or unanticipated alternatives, modifications, variations or improvements therein may be subsequently made by those skilled in the art, each of which is also intended to be encompassed by the disclosed embodiments.

What is claimed is:

1. A method to produce nylon 12, the method comprising:
converting alkyl furan compounds of formula

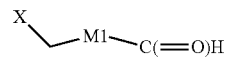

to an ester-aldehyde dimer of formula

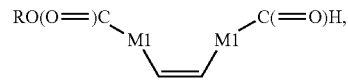

wherein X is —OH or halogen, R is $C_1$-$C_5$ alkyl, and M1 is

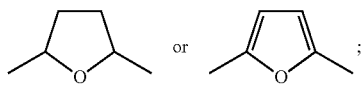

converting the ester-aldehyde dimer to an amino-ester of formula

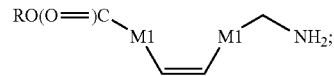

and
converting the amino-ester to nylon 12.

2. The method of claim 1, wherein converting the amino-ester to nylon 12 comprises treating the amino-ester with a halide source and hydrogen gas in a presence of a catalyst.

3. The method of claim 2, wherein converting the amino-ester to nylon 12 comprises a single pot reaction wherein:

amino-esters having M1 of

[structure: tetrahydrofuran ring with two methyl substituents]

produce intermediary products of

[structure: HO-C(=O)-[tetrahydrofuran-CH=CH-tetrahydrofuran-CH2-N(H)]n-H and RO-C(=O)-(CH2 chain)-NH2]

and amino-esters having M1 of

[structure: furan ring with two methyl substituents]

produce intermediary products of

[structure: HO-C(=O)-[furan-CH=CH-furan-CH2-N(H)]n-H and RO-C(=O)-(CH2 chain)-NH2]

where n≥2.

4. The method of claim 2, wherein treating the amino-ester comprises treating with hydrogen iodide, hydrogen chloride, hydrogen bromide, or any combination thereof in a presence of a catalyst including platinum, palladium, rhodium, ruthenium, nickel, cobalt, iron, molybdenum, iridium, rhenium, gold, or any combination thereof.

5. The method of claim 1, wherein converting the alkyl furan compounds comprises converting alkyl furan compounds including 5-chloromethyl furan compounds and 5-hydroxymethyl furan compounds; and converting the alkyl furan compounds to the ester-aldehyde dimer comprises:

converting the 5-chloromethyl furan compounds to a dimethylacetal protected Wittig reagent of formula

[structure: Ph3P+-CH2-M1-CH(OCH3)2 Cl-]

oxidizing the 5-hydroxymethyl furan compounds to produce a carboxylic acid $$HO(O=)C\text{-}M1\text{-}C(=O)H,$$

and alkylating the carboxylic acid to produce a carboxylic acid alkyl ester of formula $$RO(O=)C\text{-}M1\text{-}C(=O)H;$$

and reacting the Wittig reagent with the carboxylic acid alkyl ester to produce the ester-aldehyde dimer.

6. The method of claim 5, wherein converting the 5-chloromethyl furan compounds to the dimethylacetal protected Wittig reagent comprises treating the 5-chloromethyl furan compounds with triphenylphosphine, triarylphosphine, trialkyphosphine, diarylalkylphosphine, or any combination thereof, followed by contacting with an alcohol in a presence of an acid catalyst.

7. The method of claim 5, wherein oxidizing the 5-hydroxymethyl furan compounds comprises oxidizing the 5-hydroxymethyl furan compounds under phase transfer conditions with 4-benzoyloxy-2,2,6,6-tetramethylpiperidin-1-oxyl.

8. The method of claim 1, wherein converting the ester-aldehyde dimer to the amino-ester comprises aminating the ester-aldehyde dimer with at least one of ammonium hydroxide, ammonia, and hydroxylamine in a presence of hydrogen and a catalyst.

9. The method of claim 1, wherein converting the ester-aldehyde dimer to the amino-ester comprises:
treating the ester-aldehyde dimer with hydroxylamine to produce a corresponding ester-oxime; and
treating the ester-oxime with hydrogen and a nickel catalyst to produce the amino-ester.

10. The method of claim 1, wherein converting the ester-aldehyde dimer to the amino-ester comprises treating the ester-aldehyde dimer with a mixture of sodium cyanoborohydride, ammonium acetate, aqueous ammonium hydroxide, and an alcohol.

11. The method of claim 1, wherein converting the alkyl furan compounds comprises converting alkyl furan compounds where M1 is

[structure: furan ring with two methyl substituents]

and R is methyl; converting the alkyl furan compounds to the ester-aldehyde dimer comprises:
converting 5-chloromethylfurfural to a dimethylacetal protected Wittig reagent of formula

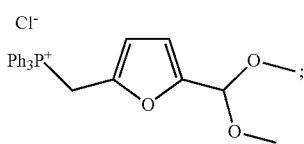

oxidizing 5-hydroxymethylfurfural to 5-formylfuroic acid, and methylating the 5-formylfuroic acid to produce methyl 5-formylfuroate of formula

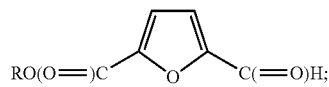

and
reacting the Wittig reagent with the methyl 5-formylfuroate to produce an ester-aldehyde dimer of formula

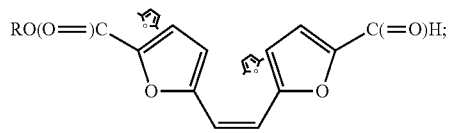

converting the ester-aldehyde dimer to the amino-ester comprises amination of the ester-aldehyde dimer of formula

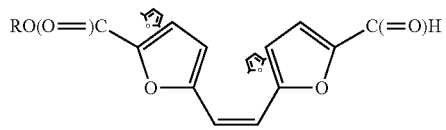

to produce an amino-ester of formula

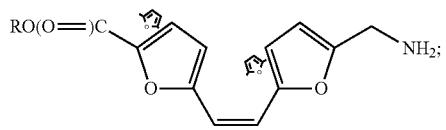

and
converting the amino-ester to nylon 12 comprises a single-pot hydrogenation-hydrodeoxygenation-polymerization reaction via intermediary products of

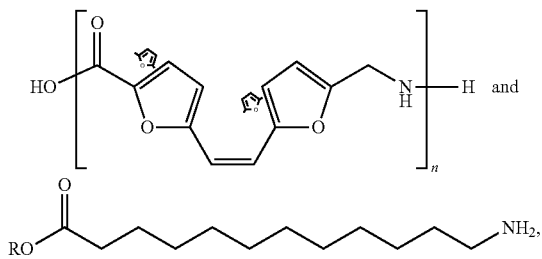

where n≥2.

12. The method of claim 1, wherein waste biomass is used to obtain the alkyl furan compounds.

13. The method of claim 12, wherein:
a first portion of the biomass is converted to 5-chloromethylfurfural;
a second portion of the biomass is converted to 5-hydroxymethylfurfural; and
wherein the 5-chloromethylfurfural and 5-hydroxymethylfurfural are converted to nylon 12.

14. The method of claim 13, wherein converting the second portion of the biomass to 5-hydroxymethylfurfural comprises heating biomass derived hexoses, cellulose, or combination thereof in a presence of at least one of an acid and a metal salt catalyst to produce the 5-hydroxymethylfurfural.

15. The method of claim 13, wherein converting the first portion of the biomass to 5-chloromethylfurfural comprises heating biomass derived hexoses, sucrose, cellulose, corn stover, or combination thereof in a presence of at least one of 1,2-dichloroethane, an alkaline salt and an acid to produce the 5-chloromethyl furfural.

16. The method of claim 13, wherein converting the 5-chloromethylfurfural and 5-hydroxymethylfurfural to nylon 12 comprises:
producing an intermediary ester-aldehyde dimer of formula

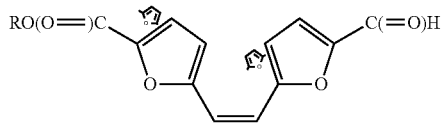

from the 5-chloromethylfurfural and 5-hydroxymethylfurfural, wherein R is C1-C5 alkyl;
converting the ester-aldehyde dimer to an amino-ester of formula

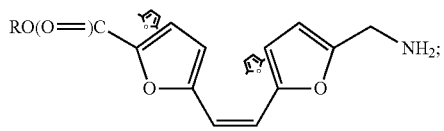

and
converting the amino-ester to nylon 12.

17. The method of claim 16, wherein converting the amino-ester to nylon 12 comprises treating the amino-ester with a halide source and hydrogen gas in a presence of a catalyst.

18. The method of claim 17, wherein converting the amino-ester to nylon 12 comprises a single pot reaction with intermediary products of

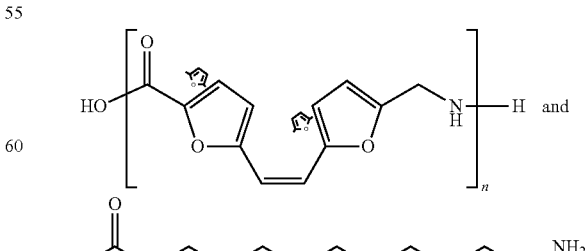

wherein n≥2.

19. The method of claim 17, wherein converting the amino-ester to nylon 12 comprises treating with hydrogen iodide, hydrogen chloride, hydrogen bromide, or a combination thereof and a catalyst comprising platinum, palladium, rhodium, ruthenium, nickel, cobalt, iron, molybdenum, iridium, rhenium, gold, or any combination thereof.

20. The method of claim 16, wherein producing the intermediary ester-aldehyde dimer comprises:
converting 5-chloromethylfurfural to a dimethylacetal protected Wittig reagent of formula

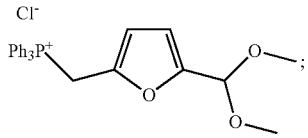

oxidizing 5-hydroxymethylfurfural to produce a carboxylic acid of formula

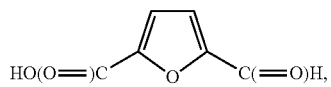

and alkylating the carboxylic acid to produce a carboxylic acid alkyl ester of formula

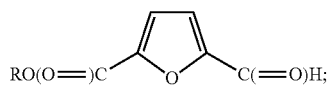

and
reacting the Wittig reagent with the carboxylic acid alkyl ester to produce the ester-aldehyde dimer.

21. The method of claim 20, wherein converting 5-chloromethylfurfural to the dimethylacetal protected Wittig reagent comprises treating the 5-chloromethyl furan with triphenylphosphine, triarylphosphine, trialkyphosphine, diarylalkylphosphine, or any combination thereof, followed by reaction with an alcohol in the presence of an acid catalyst.

22. The method of claim 20, wherein oxidizing the 5-hydroxymethylfurfural comprises oxidizing the 5-hydroxymethylfurfural with 4-benzoyloxy-2,2,6,6-tetramethylpiperidin-1-oxyl under a phase transfer condition.

23. The method of claim 16, wherein converting the ester-aldehyde dimer to the amino-ester comprises:
treating the ester-aldehyde dimer with hydroxylamine to produce a corresponding ester-oxime; and
treating the ester-oxime with hydrogen and a nickel catalyst to produce the amino-ester.

24. The method of claim 1, wherein the converting alkyl furan compounds to the ester-aldehyde dimer comprises:
converting a first alkyl furan compound having X=halogen to a dimethylacetal protected Wittig reagent of formula

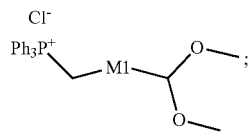

oxidizing a second alkyl furan compound having X=OH to produce a carboxylic acid of formula

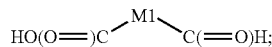

alkylating the carboxylic acid to produce a carboxylic acid alkyl ester of formula

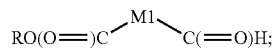

and
reacting the Wittig reagent with the carboxylic acid alkyl ester to produce the ester-aldehyde dimer.

25. The method of claim 24, wherein converting the first alkyl furan compound comprises converting 5-chloromethylfurfural and oxidizing the second alkyl furan compound comprises oxidizing 5-hydroxymethylfurfural.

26. The method of claim 24, wherein oxidizing the second alkyl furan compound comprises oxidizing 5-hydroxymethylfurfural to produce 5-formylfuroic acid and alkylating the carboxylic acid comprises methylating the 5-formylfuroic acid to produce methyl 5-formylfuroate of formula

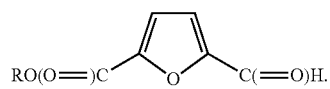

27. The method of claim 26, wherein reacting the Wittig reagent with the carboxylic acid alkyl ester comprises reacting the Wittig reagent with the methyl 5-formylfuroate to produce an ester-aldehyde dimer of formula

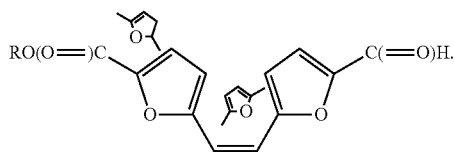

28. The method of claim 24, wherein converting the ester-aldehyde dimer to the amino-ester comprises aminating an ester-aldehyde dimer of formula

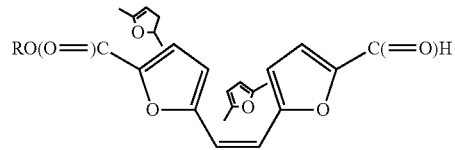

to produce an amino-ester of formula

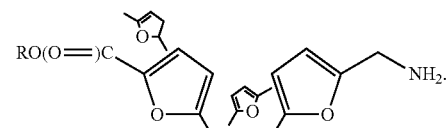

* * * * *